United States Patent
Paylian

(10) Patent No.: US 7,135,336 B1
(45) Date of Patent: Nov. 14, 2006

(54) **USE OF *XENOPUS LAEVIS* OOCYTES A MICROINCUBATORS**

(75) Inventor: Sergei Paylian, Knoxville, TN (US)

(73) Assignee: University of South Florida, Tampa, FL (US)

( * ) Notice: Subject to any disclaimer, the term of this patent is extended or adjusted under 35 U.S.C. 154(b) by 42 days.

(21) Appl. No.: 11/109,311

(22) Filed: Apr. 19, 2005

Related U.S. Application Data

(60) Provisional application No. 60/564,643, filed on Apr. 21, 2004.

(51) Int. Cl.
*C12N 5/00* (2006.01)
*C12N 5/06* (2006.01)

(52) U.S. Cl. .................. 435/325; 435/347; 435/373

(58) Field of Classification Search ............... 435/325, 435/377, 347, 373; 800/24
See application file for complete search history.

(56) References Cited

U.S. PATENT DOCUMENTS

| | | | |
|---|---|---|---|
| 6,011,197 A | 1/2000 | Strelchenko et al. | |
| 6,215,041 B1 | 4/2001 | Stice et al. | |
| 6,635,802 B1 | 10/2003 | Piedrahita et al. | |
| 6,680,199 B1 | 1/2004 | Susko-Parrish et al. | |
| 2002/0142397 A1 | 10/2002 | Collas et al. | |
| 2003/0044976 A1 | 3/2003 | Dominko et al. | |
| 2004/0072288 A1 | 4/2004 | Collas et al. | |

OTHER PUBLICATIONS

Byrne, J.A. et al. "Nuclei of adult mammalian somatic cells are directly reprogrammed to oct-4 stem cell gene expression by amphibian oocytes" *Current Biology*, 2003, 13(14):1206-1213.
Dennis, C. "Take a cell, any cell . . ." *Nature*. 2003, 426(6966):490-491.
Gonda, K. et al. "Reversible disassembly of somatic nucleoli by the germ cell proteins FRGY2a and FRGY2b" *Nature Cell Biology*, 2003, 5(3):205-210.
Kikyo, N. et al. "Active remodeling of somatic nuclei in egg cytoplasm by the nucleosomal ATPase ISWI" *Science*, 2000, 289:2360-2362.
Kirchhof, N. et al. "Expression pattern of Oct-4, in preimplantation embryos of different species" *Biol. Reprod.*, 2000, 63:1698-1705.
Morrison, S. et al. "Telomerase activity in hematopoietic cells is associated with self-renewal potential" *Immunity*, 1996, 5:207-216.
Pan, G. et al. "Stem cell pluripotency and transcription factor Oct4" *Cell Research*, 2002, 12(5-6):321-329.
Pesce, M. and Scholer, H. "Oct-4: Control of totipotency and germline determination" *Mol. Reprod. Dev.*, 2000, 55:452-457.
Schler, H. "Cell therapy: Receptor switches off pluripotency" *Applied Genetics News*, 2001 22(5):article 8.
Schmieder, S. et al. "Characterization of the putative chloride channel xClC-5 expressed in *Xenopus laevis* oocytes and comparison with endogenous chloride currents" *J. Physiol.*, 1998, 511(Pt 2):379-393.
Thomson, J. et al. "Embryonic stem cell lines derived from human blastocysis" *Science*, 1998, 282(5391):1145-1147.
Thompson, J. et al. "Isolation of a primate embryonic stem cell line" *Proc. Natl. Acad. Sci. USA*, 1995, 92:7844-7848.

*Primary Examiner*—Peter Paras, Jr.
(74) *Attorney, Agent, or Firm*—Saliwanchik, Lloyd & Saliwanchik

(57) ABSTRACT

The present invention concerns methods for de-differentiation and stabilize cells, such as progenitor cells, by introducing the cells into the cytoplasm of host oocytes, such as *Xenopus laevis* oocytes. Advantageously, this method obviates the need for any nuclear transfer procedure, which is known to disrupt the chromosomal architecture of donor and recipient cells. The present invention also concerns host oocytes encapsulating cells that have been introduced into their cytoplasm. The present invention also concerns cells that have been removed from the host oocytes.

10 Claims, 10 Drawing Sheets
(9 of 10 Drawing Sheet(s) Filed in Color)

USE OF *XENOPUS LAEVIS* OOCYTES A MICROINCUBATORS

CROSS-REFERENCE TO RELATED APPLICATION

The present application claims benefit of U.S. Provisional Application Ser. No. 60/564,643, filed Apr. 21, 2004, which is hereby incorporated by reference herein in its entirety, including any figures, tables, nucleic acid sequences, amino acid sequences, and drawings.

BACKGROUND OF THE INVENTION

Currently, scientific research is moving in three promising directions to elucidate the biomedical properties of human embryonic stem cells: a) identification of molecular events that play a key role in restricting pluripotency of embryonic stem cells, which would facilitate understanding of why pluripotency is lost in adult cells, as well as when, how, and why a stem cell differentiates into another type of cell; b) identification of an ultimate adult stem cell (body master cell), which can trans-dedifferentiate itself into virtually any of 200 types of cells in the human body; and c) identification of reprogramming factors which, under specific conditions, can orchestrate dedifferentiation of adult somatic cells into viable embryonic stem cells able to proliferate in an undifferentiated state while retaining pluripotency.

Recent studies have revealed some remarkable molecular events underlying the reprogramming of adult cells including: an activation of human Oct-4 gene, which serves as a convenient marker for nearby presence of reprogramming factors and maintains pluripotency of stem cells (Byrne J. A. et al., *Current Biology*, Jul. 15, 2003, 13(14):1206–1213); identification of germ cell nuclear factor (GCNF-receptor), which represses the Oct-4 gene, steadily decreasing its activity as embryonic stem cells differentiate and eventually restricts Oct-4's expression in the body's somatic cells, leaving expression only in the germ cell lineage (Schler H, *Applied Genetics News*, December, 2001); reversible disassembly of somatic nucleoli in *Xenopus* germ cells by the germ cell proteins FRGY2a and FRGY2b, which reversibly disassemble somatic nucleoli structure in ooplasm, independently of continuing ribosomal RNA transcription (Koichi Gonda et al., *Nature Cell Biology*, March, 2003, 5(3): 205–210); and identification of a key molecule in this process: chromatin-remodeling nucleosomal adenosine triphosphate (ATPase) ISWI, which actively erases the TATA binding protein from association with the nuclear matrix which partially explains dramatic reshuffling of egg proteins when many of them are specifically lost from nuclei, and others are taken up from the frog's ooplasm (Nobuaki K. et al., *Science*, Sep. 29, 2000: 2360–2362).

Stem cell biology is currently facing a significant ethical dilemma associated with therapeutic cloning, which involves the derivation of stem cells from human embryos. In November of 2001, the privately funded U.S. based company Advanced Cell Technology Inc. announced that it had created a cloned human embryo using a nuclear transfer procedure. It was reported that the cloned embryo reached only the six-cell stage and failed to form a blastocyst, which is necessary for harvesting of human pluripotent embryonic stem cells (CNN/SCI-Tech, Nov. 26, 2001). Reprogramming of adult human cells into embryonic stem cells (ESC) is a way to bypass creation of embryos, but these experiments usually result in hybrids containing chromosomes from both the enucleated oocyte and the adult donor cell. Such genetic mismatch cannot be used in patients.

Reprogramming of two pre-fused ES cells carried out by a nuclei separation procedure utilizing a chemical inhibitor, which prevents the nuclei from joining together, is also an inconvenient and risky technique. Several research teams recently have attempted to dedifferentiate adult cells into primordial ES cells using an ooplasm "cocktail" made from frog eggs as a source of biochemical factors, which can be responsible for reprogramming of adult cells. These experiments are promising, but the "exact nature and number of the factors is unknown" (Dennis, C. *Nature*, Dec. 4, 2003, 426(6966):490–491).

The present inventor hypothesizes that separation of cytoplasmic and nuclear materials in both donor and recipient cells during the nuclear transfer procedure or during preparation of ooplasm is an unnecessary and undesirable intervention that can disrupt very important biochemical pathways that are naturally present and responsible for reprogramming of adult donor cells. Isolation from the endogenous biochemical network can lead to an incomplete and inaccurate picture of events involved in the dedifferentiation of adult cells. This is a major disadvantage that appears to be associated with inducing stem cells to proliferate in an undifferentiated state of pluripotency.

There is a need for a methodological approach that would allow scientists to directly reprogram adult cells, thereby bypassing the need for a nuclear transfer procedure, which requires dramatic intervention in chromosomal architecture in both donor and recipient cells.

BRIEF SUMMARY OF THE INVENTION

The method of the present invention allows scientists for the first time to directly reprogram adult cells. Advantageously, the method of the invention bypasses any nuclear transfer procedure, which normally requires dramatic intervention in chromosomal architecture in both donor and recipient cells.

The method of the present invention is based on observations of specific phenomena by the present inventor and subsequently developed into a special technique which allows investigators, for the first time, to inject suspensions of viable mature (differentiated) cells into the cytoplasm of a living *Xenopus laevis* oocyte, thus creating the first "cell within a cell" model.

Using this new experimental protocol, cells can be successfully delivered into the cytoplasm of oocytes without visible damage to the integrity of the delivered cells or the recipient oocytes, which is very important. Preliminary studies have shown that relatively small injected cells (up to about 15 µm in diameter), after 24 to 28 hours of encapsulation within the host *Xenopus* oocytes, are still alive and can be successfully removed from the oocytes by rupturing oocytes with 1.5 µl injection of complete high glucose DMEM media. Combined ooplasm from 5 ruptured oocytes went through 3 step/5 min centrifugation (150 rpm, 500 rpm and 1,200 rpm). After each centrifugation, supernatant was discarded and the pellet was re-suspended in 1 ml of complete media and then cultured in 12 ml of complete high glucose DMEM supplemented with 100 mM sodium pyruvate and 200 mM L-Glutamine in 100 mm Petri dishes at 37° C./5.0% $CO_2$. The cultured cells show obvious signs of reprogramming into universal stem cells (also referred to herein as "quark-cells"), which can proliferate in the undifferentiated state without reaching confluency. These properties make the quark-cells particularly useful for therapeutic applications, such as cell therapy, and non-therapeutic applications, such as diagnostic screening methods and research pertaining to cell differentiation. For example, while encapsulated, the injected cells can be used as suitable objects for investigation of mechanisms of action of new drugs, in close vicinity of encapsulated target cells.

In preliminary studies, this system shows a capacity for rapid (e.g., within about 24 hours) and effective reprogramming of adult tissue-derived bone marrow stromal cells of transgenic (Tg) mice that express green fluorescent protein (GFP) into successfully proliferating quark-cells. Thus, using a preferred embodiment of the method of the present invention, also referred to herein as "vital intra-xenocyte injection", a practically unlimited and inexpensive source of species-specific undifferentiated quark-cells can be made available.

Preliminary studies have also shown that such a biological system can survive for many days, allowing researchers to be able to introduce substances of interest directly into the vicinity of the *Xenopus* oocyte-encapsulated cells, and subsequently remove the cells for culturing. Using specific external agonists, this system provides investigators with a unique opportunity to manipulate the biochemical machinery of encapsulated cells through the biochemical machinery of the hosting oocyte, without unnecessarily interfering with the normal communications that take place inside both types of cells (the host oocyte and the encapsulated cell).

Any developmental stage of oocyte can be utilized, so long as the oocyte's cytoplasmic milieu retains the ability to de-differentiate, re-program, and/or stabilize the encapsulated cell or cells. The cell or cells are introduced into the oocyte for a period of time sufficient to achieve the desired degree of de-differentiation, reprogramming, and/or stabilization.

For many pharmacological companies, this method of the present invention will open new broad opportunities for investigating the mechanisms of action of new drugs, using "natural means" for their delivery into the host oocyte and encapsulated cell(s).

In clinics, oocytes encapsulating quark-cells can serve as "natural" delivery capsules for damaged body organs helping them to overcome problems associates with tissue rejection and use of immunosuppressive drugs.

The method of the present invention can be automated for stem cell research and for commercial use and should dramatically reduce labor and material expenses, such as those normally associated with nuclear transfer procedures. Such expenses typically include costs for culture media, expensive chemicals, and electricity (e.g., use of hoods and lights in the culture rooms). Advantageously, because simple frog oocytes can be utilized in the present invention to serve as micro-incubators and "natural capsules" for introduced cells needing to be reprogrammed, the interest of economy is served.

The present invention also offers fascinating potential in illuminating such a "dark" field of biology as the electrophysiology of stem cells. In another aspect of the invention, a primary frog oocyte membrane-specific antibody is introduced into the cytoplasm of a living oocyte, which will recognize the inner lining of its membrane; and a secondary antibody is introduced into the cytoplasm which will be able to distinguish both the "primary" membrane-bound antibody of the oocyte, and a specific membrane-bound antibody of the oocyte, and a specific membrane bound protein of stem cells (Schmieder, S. et al. *J. Physiol.*, 1998, 511(Pt 2):379–393, which is incorporated herein by reference in its entirety). In this case, a sandwich-like structure of fixed intra-oocyte layers of stem cells can be achieved, thereby opening the possibility for their electronic detection through two electrode voltage-clamp recordings, which can include comparative analysis of parallel current recordings both from a single oocyte and from oocytes encapsulating quark cells.

The present invention will also be attractive to the National Aeronautics and Space Administration (NASA) biomedical program because the system will allow investigators to answer many fundamental questions associated with influence of gravitational force on tissue and organ formation. In this case, even in the absence of gravity, oocytes will still be able to hold injected stem cells inside their cytoplasm, restricting them from undesirable motions, and simultaneously allowing them to be exposed to weightlessness.

In another aspect, the present invention provides an isolated host oocyte having one or more cells introduced into the host oocyte's cytoplasm, wherein the cell or cells encapsulated within the ooplasm is capable of becoming de-differentiated, re-programmed, and/or stabilized (from a cell fate or potency perspective). In one embodiment, the host oocyte is an amphibian oocyte. Preferably, the amphibian oocyte is a frog oocyte. More preferably, the oocyte is a *Xenopus laevis* oocyte.

In another aspect, the present invention provides a cell (also referred to herein as a quark-cell) that has been de-differentiated, re-programmed, and/or stabilized according to any of the methods of the invention, or combinations of methods of the invention. In one embodiment, the cell has been introduced into a host oocyte according to the method of the invention, and subsequently removed from the cytoplasm of the host oocyte.

In another aspect, the present invention provides compositions comprising host oocytes encapsulating one or more cells, and a pharmaceutically acceptable carrier. In another aspect, the present invention provides compositions comprising cells that have been removed from the host oocytes following de-differentiation, re-programming, and/or stabilization. In a further aspect, the present invention provides methods of cell transplantation involving the administration of such cells to a human or non-human animal. In one embodiment of the cell transplantation method, the cells are administered to a human or non-human animal within a pharmaceutical composition for cell therapy. In another embodiment of the cell transplantation method, the cells are administered to a human or non-human animal for a non-therapeutic objective, such as the study of cell migration and/or cell fate in vivo.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows the hosting oocyte under regular light, illuminated from above with sharply distinguished animal and vegetal sides. FIG. 3 shows the same oocyte illuminated from beneath with high intensity red light. FIG. 4 shows the same oocyte emitting green light under a fluorescent microscope. All three micrographs were taken after 72 hours of BMSC encapsulation inside hosting oocytes.

FIG. 17 shows "black holes" which will soon "explode" in the form of new cells. When compression is in progress, the darker the "hole" appears, the more bio-quarks are attracted.

BRIEF DESCRIPTION OF THE SEQUENCES

Figure 1:
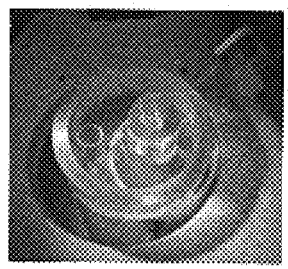
FIG. 1 shows an apparatus for perfusion of oocytes.

SEQ ID NO: 1 is a green fluorescent protein (GFP) hexapeptide.

DETAILED DESCRIPTION OF THE INVENTION

The subject invention pertains to a method of de-differentiating, re-programming, and/or stabilizing a cell or cells by introducing the cell or cells into an oocyte, such as a *Xenopus laevis* oocyte. The method reliably redirects de-differentiation of cells, such as adult somatic cells, into a stem-like cell type. Differentiated cells or undifferentiated cells can be introduced into the oocytes. For example, undifferentiated or de-differentiated cells can be introduced into oocytes for the purpose of stabilization (i.e., maintenance of the de-differentiated state). Optionally, the resulting cells can then be induced to differentiate into a desired cell type which may be wholly different from the cells' previous state or fate.

The host oocyte should be of sufficient size to accommodate the one or more cells to be introduced therein. For example, in one embodiment, the oocyte is 0.5 to 2 mm in diameter. In another embodiment, the oocyte is 1.0 to 1.2 mm in diameter. Preferably, the host oocyte used in the methods of the subject invention is an amphibian oocyte, such as a frog oocyte. More preferably, the host oocyte is a *Xenopus laevis* oocyte. In one embodiment, the cell(s) to be encapsulated is 30 μm or less in diameter. In another embodiment, the cell(s) to be encapsulated is 20 μm or less in diameter. Preferably, the cell(s) to be encapsulated is 15 μm or less in diameter.

In an exemplified embodiment, intra-oocyte injections of a suspension of C57 transgenic (Tg) mice bone marrow stromal cells (BMSC) expressing green fluorescent protein (GFP) is carried out. Under certain conditions, frog oocytes, such as *Xenopus laevis* oocytes, are capable of forming a super seal in a hole of its membrane that is caused by a needle of an unusually large diameter. Any technique that introduces the cell or cells into the oocyte without permanently damaging the structural integrity of the oocyte membrane can be utilized, however. The present inventor has successfully delivered small (up to about 15 μM) mature cells into the cytoplasm of larger (1–1.2 mm) embryonic cells, thus creating a "cells within a cell" system. This new methodological approach allows dedifferentiation of progenitor cells into universal primordial "quark-cells" bypassing the nuclear transfer procedure and should significantly contribute to human stem cell therapy.

The cells introduced into oocytes according to the method of the invention can range in plasticity from totipotent or pluripotent stem cells (e.g., adult or embryonic), precursor or progenitor cells, to highly specialized cells, such as those of the central nervous system (e.g., neurons and glia). Stem cells can be obtained from a variety of sources, including embryonic tissue, fetal tissue, adult tissue, umbilical cord blood, peripheral blood, bone marrow, and brain, for example.

Optionally, according to the method of the present invention, cells can be modified before or after they are introduced into the cytoplasm of the oocyte. For example, cells can be modified through genetic modification (e.g., genetic engineering), differentiated with differentiation agents (e.g., trophic factors), or with adjuvants (e.g., chemotherapies, radiation therapies, and the like), before or after intra-oocyte injection.

As will be understood by one of skill in the art, there are over 200 cell types in the human body. It is believed that the methods of the subject invention can be used to de-differentiate, reprogram, and/or stabilize any of these cell types for therapeutic or other purposes. For example, any cell arising from the ectoderm, mesoderm, or endoderm germ cell layers can be introduced into an oocyte and de-differentiated, reprogrammed, and/or stabilized according to the method of the subject invention. It will be understood by one of skill in the art that the methods of the present invention are also applicable for veterinary purposes. For example, cells of non-human animals can find application either in human or animal patients (e.g., veterinary uses).

The methods of the subject invention are useful for de-differentiating, re-programming, and/or stabilizing any cell type, for therapeutic or other purposes. For example, cells that can be introduced into oocytes according to the methods of the subject invention include those cells arising from the ectoderm, mesoderm, or endoderm germ cell layers. Such cells include, but are not limited to, neurons, glial cells (astrocytes and oligodendrocytes), muscle cells (e.g., cardiac, skeletal), chondrocytes, fibroblasts, melanocytes, Langerhans cells, keratinocytes, endothelial cells, epithelial cells, pigment cells (e.g., melanocytes, retinal pigment epithelial (RPE) cells, iris pigment epithelial (IPE) cells), hepatocytes, microvascular cells, pericytes (Rouget cells), blood cells (e.g., erythrocytes), cells of the immune system (e.g., B and T lymphocytes, plasma cells, macrophages/monocytes, dendritic cells, neutrophils, eosinophils, mast cells), thyroid cells, parathyroid cells, pituitary cells, pancreatic cells (e.g., insulin-producing β cells, glucagon-producing a cells, somatostatin-producing δ cells, pancreatic polypeptide-producing cells, pancreatic ductal cells), stromal cells, Sertoli cells, adipocytes, reticular cells, rod cells, and hair cells. Other examples of cell types with which the invention can be performed include those disclosed by Spier R. E. et al., eds., (2000) *The Encyclopedia of Cell Technology*, John Wiley & Sons, Inc., and Alberts B. et al., eds., (1994) *Molecular Biology of the Cell*, $3^{rd}$ ed., Garland Publishing, Inc., e.g., pages 1188–1189. Table 1 contains a non-exhaustive list of cells that may be de-differentiated, re-programmed, and/or stabilized in accordance with the present invention.

Methods and markers commonly used to identify stem cells and to characterize differentiated cell types are described in the scientific literature (e.g., Stem Cells: Scientific Progress and Future Research Directions, Appendix E1–E5, report prepared by the National Institutes of Health, June, 2001, which is incorporated herein by reference in its entirety). Such methods and markers can be used to characterize cells before and/or after de-differentiation or re-programming using the present invention. The list of adult tissues reported to contain stem cells is growing and includes bone marrow, peripheral blood, umbilical cord blood, brain, spinal cord, dental pulp, blood vessels, skeletal muscle, epithelia of the skin and digestive system, cornea, retina, liver, and pancreas.

Depending upon cell type, differentiation of the cells can be induced by any method known in the art that activates the cascade of biological events that lead to cell growth. For example, cells can be induced to differentiate by plating the cells on a fixed substrate, such as a flask, plate, or coverslip, or a support of collagen, fibronectin, laminin, or extracellular matrix preparation such as MATRIGEL (Collaborative Research), or removal of conditioned medium. Cells can be incubated in dishes and on cover slips coated with MATRIGEL to allow gellification and subsequently seeded onto the treated surface (Cardenas, A. M. et al., *Neuroreport.*, 1999, 10:363–369). Differentiation can be induced by transfer to GM with 1% bovine serum and 10 μg/ml of both insulin and transferrin, wherein differentiating media is F12/D supplemented with 1% bovine serum and 1% stock supplement (Liberona, J. L. et al., *Muscle &Nerve*, 1998, 21:902–909).

Cells can be stimulated to differentiate by contact with one or more differentiation agents (e.g., trophic factors, hormonal supplements), such as forskolin, retinoic acid, putrescin-transferrin, cholera toxin, insulin-like growth factor (IGF), transforming growth factor (e.g., TGF-a, TGF-β), tumor necrosis factor (TNF), fibroblast growth factor (FGF), epidermal growth factor (EGF), granulocyte macrophage-colony stimulating factor (GM-CSF), hepatocyte growth factor (HGF), hedgehog, vascular endothelial growth factor (VEGF), thyrotropin releasing hormone (TRH), platelet derived growth factor (PDGF), sodium butyrate, butyric acid, cyclic adenosine monophosphate (cAMP), cAMP derivatives (e.g., dibutyryl cAMP, 8-bromo-cAMP) phosphodiesterase inhibitors, adenylate cyclase activators, prostaglandins, ciliary neurotrophic factor (CNTF), brain-derived neurotrophic factor (BDNF), neurotrophin 3, neurotrophin 4, interleukins (e.g., IL-4), interferons (e.g., interferon-gamma), leukemia inhibitory factor (LIF), potassium, amphiregulin, dexamethasone (glucocorticoid hormone), isobutyl 3-methyulxanthine, somatostatin, lithium, and growth hormone.

The subject invention provides a ready source of cells for research, including pharmacological studies for the screening of various agents, and toxicologic studies for the cosmetic and pharmaceutical industries. The cells of the subject invention can be used in methods for determining the effect of a synthetic or biological agent on cells. The term "biological agent" refers to any agent of biological origin, such as a virus, protein, peptide, amino acid, lipid, carbohydrate, nucleic acid, nucleotide, drug, pro-drug, or other substance that may have an effect on cells, whether such effect is harmful, beneficial, or otherwise. Thus, the cells of the present invention can be used for screening agonists and antagonists of compounds and factors that affect the various metabolic pathways of a specific cell, for example. The choice of cell will depend upon the particular agent being tested and the effects one wishes to achieve.

The cells with which the methods of the invention can be used can be of any animal species; e.g., mammals, avians, reptiles, fish, and amphibians. Examples of mammalian cells that can be de-differentiated and, optionally, re-differentiated by the present invention include but are not limited to human and non-human primate cells, ungulate cells, rodent cells, and lagomorph cells. Primate cells with which the invention may be performed include but are not limited to cells of humans, chimpanzees, baboons, cynomolgus monkeys, and any other New or Old World monkeys. Ungulate cells with which the invention may be performed include but are not limited to cells of bovines, porcines, ovines, caprines, equines, buffalo and bison. Rodent cells with which the invention may be performed include but are not limited to mouse, rat, guinea pig, hamster and gerbil cells. Rabbit cells are an example of cells of a lagomorph species with which the invention may be performed.

Specific somatic cells with which the invention can be performed are human skin fibroblasts transgenic for mouse Oct4 promoter-driven GFP gene. The mouse Oct4 promoter can drive GFP expression in porcine and bovine preimplantation embryos (Kirchhof, et al., *Biol. Reprod.*, 2000, 63:1698). Oct4 is the only known molecular marker of pluripotency that has been shown to be absolutely required for normal development of pluripotent mammalian inner cell mass during early embryogenesis. Pluripotent embryos and embryonic stem cells as well as embryonic-derived tumors are the only tissues in mammals that show expression of this gene (Scholer et al., *Cell*, 1991, 66:291; Pesce and Scholer, *Mol. Reprod. Dev.*, 2000, 55:452). For example, the mouse Oct4 promoter and its regulatory 5'UTR (8 Kb-H. Scholer) can be used to direct expression of GFP gene as a marker of successfully de-differentiated cells.

Embryonic stem cells retain their pluripotency in vitro when maintained on inactivated fetal fibroblasts in culture. More recently, it has been reported that human embryonic stem cells can successfully be propagated on MATRIGEL in a medium conditioned by mouse fetal fibroblasts. Human stem cells can be grown in culture for extended period of time (Thomson and Marshall, *Curr. Top. Dev. Biol.*, 1998, 38:133) and remain undifferentiated under specific culture conditions. De-differentiated cells are expected to display many of the same requirements as pluripotent stem cells and can be cultured under conditions used for embryonic stem cells.

Various methods for evaluating de-differentiated cells can be utilized. For example, monitoring changes in the cells' phenotype and characterizing their gene expression and protein production can be carried out (using methods such as RT-PCR and/or immunocytochemistry). Live time-lapse video imaging can be used to monitor the uptake of agents, changes in cell morphology upon hybridization (or lack thereof), and dynamics of changes induced as well as GFP transgene fluorescence. Screening results can be compared to results obtained with undifferentiated, pluripotent control cells such as monkey parthenogenetic stem cells (ADVANCED CELL TECHNOLOGY), or human embryonic stem cells (Wisconsin Alumni Research Foundation, Madison, Wis. and Geron, Inc). Stem cell markers and morphometric and growth characteristics of parthenogenetic cynomolgous monkey embryonic stem cells match with those published by Thomson et al. (*Science*, 1998, 282:5391) for human embryonic stem cells obtained from in vitro fertilized human blastocysts.

The expression of the following genes of de-differentiated cells and human embryonic stem-like cells can be compared: alkaline phosphatase, Oct4, SSEA-3, SSEA-4, TR-1-60 and TR-1-81 (Thomson et al., *Proc. Natl. Acad. Sci. USA*, 1995, 92:7844; Thomson et al., *Science*, 1998, 282:5391). Assays designed to detect expression of genes specific to the given cell type can be used to confirm the presence of expression in the cells prior to hybridization, and to confirm the absence of expression after hybridization. Self-renewing capacity, marked by induction of telomerase activity, is another characteristic of stem cells that can be monitored in de-differentiating cells (Morrison et al., *Immunity*, 1996, 5:207).

The de-differentiated, re-programmed, and/or stabilized cells of the subject invention can be administered as cell therapy to alleviate the symptoms of a wide variety of disease states and pathological conditions, in various stages of pathological development. For example, cells of the subject invention can be used to treat acute disorders (e.g., stroke or myocardial infarction), and administered acutely, subacutely, or in the chronic state. Similarly, the cells of the subject invention can be used to treat chronic disorders (e.g., Parkinson's disease, diabetes, or muscular dystrophy), and administered preventatively and/or prophylactically, early in the disease state, in moderate disease states, or in severe disease states. For example, the cells of the subject invention can be administered to a target site or sites on or within a patient in order to replace or compensate for the patient's own damaged, lost, or otherwise dysfunctional cells. This includes infusion of the cells into the patient's bloodstream. The cells to be administered can be cells of the same cell type as those damaged, lost, or otherwise dysfunctional, or a different cell type. For example, insulin-producing pancreatic islet beta cells supplemented with other types of cells of the subject invention can be administered to the liver (Goss, J. A., et al., *Transplantation*, Dec. 27, 2002, 74(12): 1761–1766). As used herein, patients "in need" of the cells of the subject invention include those desiring elective surgery, such as elective cosmetic surgery.

The de-differentiated, re-programmed, and/or stabilized cells of the subject invention can be administered as autografts, syngeneic grafts, allografts, and xenografts, for example. As used herein, the term "graft" refers to one or more cells intended for implantation within a human or other animal. Hence, the graft can be a cellular or tissue graft, for example.

The de-differentiated, re-programmed, and/or stabilized cells of the subject invention can be administered to a patient by any method of delivery, such as intravascularly, intracranially, intracerebrally, intramuscularly, intradermally, intravenously, intraocularly, orally, nasally, topically, or by open surgical procedure, depending upon the anatomical site or sites to which the cells are to be delivered. Cells can be administered in an open manner, as in the heart during open heart surgery, or in the brain during stereotactic surgery, or by intravascular interventional methods using catheters going to the blood supply of the specific organs, or by interventional methods such as intrahepatic artery injection of pancreatic cells for diabetics.

The cells of the subject invention can be administered to a patient in isolation or within a pharmaceutical composition comprising the cells and a pharmaceutically acceptable carrier. As used herein, a pharmaceutically acceptable carrier includes solvents, dispersion media, coatings, antibacterial and antifungal agents, isotonic agents, and the like. Pharmaceutical compositions can be formulated according to known methods for preparing pharmaceutically useful compositions.

The cells of the subject invention can be administered on or within a variety of carriers that can be formulated as a solid, liquid, semi-solid, etc. For example, genetically modified cells or non-genetically modified cells can be suspended within an injectable hydrogel composition (U.S. Pat. No. 6,129,761) or encapsulated within microparticles (e.g., microcapsules) that are administered to the patient and, optionally, released at the target anatomical site (Read T. A. et al., *Nature Biotechnology*, 2001, 19:29–34, 2001; Joki T. et al., *Nature Biotechnology*, 2001, 19:35–38; Bergers G. and Hanahan D., *Nature Biotechnology*, 2001, 19:20–21; Dove A. *Nature Biotechnology*, 2002, 20:339–343; Sarkis R. *Cell Transplantation*, 2001, 10:601–607).

Carriers are preferably biocompatible and optionally biodegradable. Suitable carriers include controlled release systems wherein the cells and/or the biological factors produced by the cells are released from the carrier at the target anatomic site or sites in a controlled release fashion. The mechanism of release can include degradation of the carrier due to pH conditions, temperature, or endogenous or exogenous enzymes, for example.

The cells of the invention can be administered in or on various scaffolds, such as synthetic or biological tissue scaffolds (Griffith G. and Naughton G., *Science*, 2002, 295:1009–1013; Langer R., *Stem Cell Research News*, Apr. 1, 2002, pp. 2–3). Porous scaffold constructs can be composed of a variety of natural and synthetic matrices, such as biominerals (e.g., calcium phosphate) and polymers (e.g., alginate) that are optionally cross-linked, and serve as a template for cell proliferation and ultimately tissue formation. Three-dimensional control of pore size and morphology, mechanical properties, degradation and resorption kinetics, and surface topography of the scaffold can be optimized for controlling cellular colonization rates and organization within an engineered scaffold/tissue construct. In this way, the morphology and properties of the scaffold can be engineered to provide control of the distribution of bioactive agents (e.g., proteins, peptides, etc.) and cells. In addition to use as vehicles for delivery of the cells, scaffolds can be utilized to grow the cells in vitro.

In the transplantation method of the invention, cells of the subject invention are preferably administered to a patient in an amount effective to provide a therapeutic benefit. However, it should also be understood that genetically modified or non-genetically modified cells may be administered for non-therapeutic purposes, such as the study of cell migration and/or cell fate. For example, a cell of the invention (e.g., a quark-cell) can be genetically modified with a marker gene to track the cell in vivo. A "therapeutically effective amount" is that amount effective to treat a pathological condition. For purposes of the subject invention, the terms "treat" or "treatment" include preventing, inhibiting, reducing the occurrence of and/or ameliorating the physiological effects of the pathological condition to be treated. Preferably, the cells are administered to the patient in an amount within the range of about $10^4$ to about $10^{10}$ cells. More preferably, the cells are administered to the patient in an amount within the range of about $10^7$ to about $10^{10}$ cells. Doses of cells can be determined by one of ordinary skill in the art, with consideration given to such factors as cell survival rate following administration, the number of cells necessary to induce a physiologic response in the normal state, and the species of the patient.

Optionally, cells may be genetically modified before or after de-differentiation, re-programming, and/or stabilization. The term "genetic modification" as used herein refers to the stable or transient alteration of the genotype of a cell of the subject invention by intentional introduction of exogenous nucleic acids by any means known in the art (including for example, direct transmission of a polynucleotide sequence from a cell or virus particle, transmission of infective virus particles, and transmission by any known polynucleotide-bearing substance) resulting in a permanent or temporary alteration of genotype. The nucleic acids may be synthetic, or naturally derived, and may contain genes, portions of genes, or other useful polynucleotides. The cells may be genetically modified to produce a therapeutic or non-therapeutic gene product. The term "genetic modification" is not intended to include naturally occurring alterations such as that which occurs through natural viral activity, natural genetic recombination, or the like. However, such naturally altered cells can also be utilized for the methods of the subject invention. It is also contemplated that the host oocyte encapsulating the cell to be de-differentiated, re-programmed, or stabilized can be genetically modified.

Exogenous nucleic acids can be introduced into a cell of the subject invention by viral vectors (retrovirus, modified herpes virus, herpes virus, adenovirus, adeno-associated virus, and the like) or direct DNA transfection (lipofection, calcium phosphate transfection, DEAE-dextran, electroporation, and the like), for example.

As used herein, the term "differentiated" refers to those cells that maintain in culture all, or a substantial amount of, their specialized structure and function (such as morphology, electrophysiological characteristics, one or more phenotypic markers, etc.) typical of the cell type in vivo. Partially differentiated cells maintain less than a substantial amount of their full complement of specialized structure and/or function. The term "de-differentiated" refers to cells that have lost one or more features of their specialized structure and function (such as morphology, electrophysiological characteristics, one or more phenotypic makers, etc.) using the microincubator or method of the invention. The term "re-programmed" refers to cells that have an altered potency or phenotype. For example, a cell may be re-programmed to differentiate along a similar cell lineage or trans-differentiate along a wholly different cell lineage. The term "stabilized" refers to cells that have been effectively "frozen" in a dormant, undifferentiated state or partially differentiated state. Stabilized cells can be removed from their host oocyte (becoming quark-cells as described herein) and induced to differentiate along a desired path.

As used herein, the term "stem cell" is an unspecialized cell that is capable of replicating or self renewal, and developing into specialized cells of a variety of cell types. The product of a stem cell undergoing division is at least one additional stem cell that has the same capabilities of the originating cell. For example, under appropriate conditions, a hematopoietic stem cell can produce a second generation stem cell and a neuron. Stem cells include embryonic stem cells (e.g., those stem cells originating from the inner cells mass of the blastocyst) and adult stem cells (which can be found throughout the more mature animal, including humans). As used herein, stem cells are intended to include those stem cells found in animals that have matured beyond the embryonic stage (e.g., fetus, infant, adolescent, juvenile, adult, etc.). The list of tissues reported to contain stem cells is growing and includes, for example, bone marrow, peripheral blood, brain, spinal cord, umbilical cord blood, amniotic fluid, placenta, dental pulp, blood vessels, skeletal muscle, epithelia of the skin and digestive system, cornea, retina, liver, and pancreas.

As used herein, the term "progenitor cell" (also known as a precursor cell) is unspecialized or has partial characteristics of a specialized cell that is capable of undergoing cell division and yielding two specialized cells. For example, a myeloid progenitor/precursor cell can undergo cell division to yield two specialized cells (a neutrophil and a red blood cell).

As used herein, the term "phenotype" refers to all the observable characteristics of a cell (or organism); its shape (morphology); interactions with other cells and the non-cellular environment (e.g., extracellular matrix); proteins that appear on the cell surface (surface markers); and the cell's behavior (e.g., secretion, contraction, synaptic transmission).

As used herein, the terms "administer", "apply", "treat", "transplant", "implant", "deliver", or "introduce", and grammatical variations thereof, are used interchangeably to provide cells of the subject invention to a patient or to a host oocyte according to the methods of the invention. For example, one or more cells (such as mature, differentiated cells; progenitor cells; stem cells) may be introduced into a host oocyte by injection into the oocyte's cytoplasm (ooplasm).

The terms "cell" and "cells" are used interchangeably herein to refer to a single cell or plurality of cells (i.e., at least one cell).

The pharmaceutical compositions of the subject invention can be formulated according to known methods for preparing pharmaceutically useful compositions. Formulations are described in a number of sources which are well known and readily available to those skilled in the art. For example, *Remington's Pharmaceutical Sciences* (Martin E. W., 1995, Easton Pa., Mack Publishing Company, 19$^{th}$ ed.) describes formulations which can be used in connection with the subject invention. Formulations suitable for parenteral administration of cells of the invention include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The terms "comprising", "consisting of" and "consisting essentially of" are defined according to their standard meaning. The terms may be substituted for one another throughout the instant application in order to attach the specific meaning associated with each term. The phrases "isolated" or "biologically pure" refer to material that is substantially or essentially free from components which normally accompany the material as it is found in its native state. For example, host oocytes may be isolated prior to introduction of one or more cells into the oocytes.

As used in this specification and the appended claims, the singular forms "a", "an", and "the" include plural reference unless the context clearly dictates otherwise. Thus, for example, a reference to "an oocyte" includes more than one such oocyte, and the like.

The practice of the present invention can employ, unless otherwise indicated, conventional techniques of molecular biology, microbiology, recombinant DNA technology, electrophysiology, and pharmacology, that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover ed. 1985); Perbal, B., A Practical Guide to Molecular Cloning (1984); the series, Methods In Enzymology (S. Colowick and N. Kaplan eds., Academic Press, Inc.); Transcription and Translation (Hames et al. eds. 1984); Gene Transfer Vectors For Mammalian Cells (J. H. Miller et al. eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. eds. (1991) IRL Press), each of which is hereby incorporated herein by reference in its entirety).

Following are examples that illustrate materials, methods, and procedures for practicing the invention. The examples are illustrative and should not be construed as limiting.

Materials and Methods

*Xenopus laevis* Oocytes. All experiments were carried out in strict accordance with IACUC policies of animal care and use of University of South Florida PHS#A4100; USDA#58; AAALAC#434. South African clawed, egg bearing frogs (*Xenopus laevis*) (XENOPUS EXPRESS Co., Plant City, Fla.) were adapted to the new environment for 2–3 weeks. Prior to surgery, frogs were anesthetized in plastic container in 1 L of 0.2% MS222 (tricane, SIGMA, St. Louis, Mo., cat.# A5040) for up to 20 minutes and then placed on a dissecting pan filled with ice. A small incision (0.5 cm) was made through the skin layer and then the muscle layer. Bags of the ovary were surgically removed and placed into oocyte washing (OW) solution containing: 82.5 mM NaCl, 5.0 mM HEPES, 2.5 mM KCl, 1 mM $MgCl_2$, 1.0 mM $Na_2HPO_4$, 0.5% penicillin/streptomycin antibiotics mixture and titrated to pH 7.4. Bags containing oocytes were minced with multiple rinsing in OW. After the final rinse, the remaining follicular cell layer, which wrapped the oocytes, and the rest of the connective tissue, was digested by placing material into 0.2% collagenase solution for 1 hour at room temperature on a rotary mixer. This procedure was followed by multiple rinsing in OW solution and then holding buffer (HB)=OW+1.0 mM $CaCl_2$, +2.5 mM pyruvate +5% heat-inactivated horse serum pH 7.4. Defolliculated oocytes in the final stage of maturity, with sharply distinguished animal and vegetal hemispheres, were collected into HB solution and incubated at 18° C. in a Model 2005 Low Temperature Incubator for 24 hours before they were injected with suspension of BMS cells derived from C57 Tg-mice.

Bone Marrow Stromal Cells (BMSC). $20^{th}$ passage GFP-expressing BMSC from adult female C57 Tg-mice were kindly prepared and provided in the amount of $10^6$ cells/ml by Dr. S. Song and Dr. J. Sanchez-Ramos (Department of Neurology, Center for Aging and Brain Repair, University of South Florida College of Medicine). Viability of cells was 96.3% (134/5).

Intra-Oocyte Injection. Cell suspension delivery needles 20–25 μm in diameter were constructed of 1.0 mm×0.5 mm, 6" glass standard filaments (A-M Systems, Inc., Carlsborg Wash., cat#626500). The approximate diameter of the tip was measured by placing it between closest (40 μm) grids of hemocytometer (FISHER SCIENTIFIC cat. # 0267110). The basic apparatus for oocyte injection consisted of a M3301 type Manual Micromanipulator (WPI Co.), WILD M3C microscope (Heerbrugg, Switzerland), and Picospritzel II pneumatic pump (CV Co.). Before injection, all oocytes were pierced with a thin needle to increase membrane tension. One minute after membrane activation 50 nl of suspension of BMSC was delivered to animal part of each oocyte. The approximate amount of cells per injection (55 cells) was calculated by pumping out 3 ul of cell suspension out of needle into 0.5 ml eppendorf tube containing 3 ul of 0.4% trypane blue. Next, 6 μl of this mixture was applied to hemocytometer and amount of cells were calculated in the field of Zeiss Invertoscope. Oocytes injected with BMSC and non-injected control oocytes were incubated in 60×15 mm style polystyrene Falcon culture plates filled with 8 ml of HB and divided into three time groups corresponding to 24 hours, 48 hours, and 72 hours of intra-oocyte incubation.

Microscopy. In one set of experiments, oocytes from each time group were examined under an Olympus IX71 fluorescent microscope for possible detection of GFP caused fluorescence by passing maximum intensity blue light through the body of host oocytes, after which ooplasm of each photogenic oocyte was removed and cultured to detect corresponding to each level of fluorescence amount of viable post-encapsulated BMS cells in culture. The rest of the oocytes were split into two groups corresponding to two different BMSC culturing procedures: oocytes from the first group, after 24 hours, 48 hours, and 72 hours of intra-oocyte incubation were destroyed by injection of 1.5 μl of complete high glucose DMEM media containing 100 mM sodium pyruvate and 200 mM L-Glutamine by use of 20 μm diameter needle in a specially designed 50 μl capacity chamber (shown in FIG. 1), which before perfusion was pre-filled with 50 μl of the same media.

In such a way, for each intra-oocyte incubation time, an ooplasm of 5 oocytes was collected into an 1.5 ml Eppendorf tube in a total volume of 1 ml on ice. Combined ooplasm went through 3 step/5 minute centrifugation (150 rpm, 500 rpm and 1,200 rpm). After each centrifugation, supernatant was discarded and the pellet was re-suspended in 1 ml of complete media and then cultured in 12 ml of complete high glucose DMEM supplemented with 100 mM sodium pyruvate and 200 mM L-Glutamine in 100 mm Petri dishes at 37° C./5.0% $CO_2$. In the second group, perfusate was transferred directly into 100 mm culture plates bypassing centrifugation steps and cells were maintained under the same conditions as BMSC from the first group. Altogether, 8 plates with cultured BMSC were taken into experiments. Developmental events in cell cultures throughout the entire experiment were monitored both by light and fluorescence microscopes. Several viability tests were performed concurrently with the other experiments. Cells of the SH-EP1 human neuroblastoma cell line were kindly provided by C. Rogers (University of South Florida, Department of Pharmacology).

Electrophysiological Recordings. The last set of experiments was designed to investigate survival and lifespan differences between frog oocytes injected with BMSC and non-injected oocytes. Both groups were carefully maintained under the same conditions for a prolonged period of time. At late stages of the longevity test, when all oocytes in the control group died, the α4/β2 RNA of human nicotinic receptors (HNR) was injected into long-lived donor oocytes to check the performance of their biochemical machinery through expression of human α4/β2 nicotinic receptors in the oocyte membrane. For construction of a 12 point acetylcholine chloride concentration response curve, two electrode voltage clump recordings were used on OPUS EXPRESS equipment designed for 8 parallel recordings (AXON INSTRUMENTS, Foster City, Calif.). Agonist was added in progressively increased concentration from 100 nM up to 3 mM, with a 5 minute rinse between each application. Whole cell currents were measured at room temperature, 48 hours after RNA injection.

EXAMPLE 1

Figure 2:
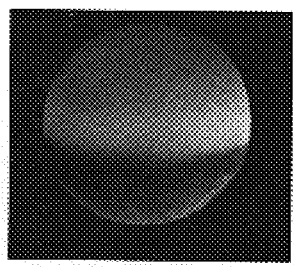
FIGS. 2–4 show the same oocyte containing a bone marrow stromal cell (BMSC) under various conditions.
Figure 3:
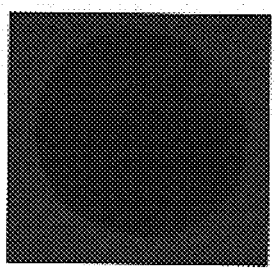
Figure 4:
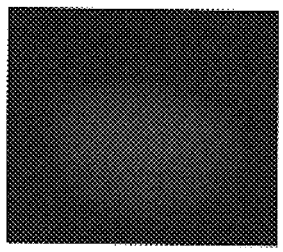

Encapsulation of Bone Marrow Stromal Cells
(BMSC) within *Xenopus laevis* Oocytes In order to show that injected BMSC are physically present inside the host cells, three pictures of the same recipient oocyte with slightly changed orientation in space for better pictures were taken. FIG. 2 shows the hosting oocyte in regular light, illuminated from the top with sharply distinguished animal and vegetal sides. FIG. 3 shows the same oocyte, but illuminated from beneath with high intensity red light. FIG. 4 shows the same oocyte emitting green light under a fluorescent microscope. Glowing occurs in the animal part of hosting oocyte, i.e., in the part where donor cells were originally injected. The vegetal part of the same oocyte in this photograph remains invisible. All three photographs were taken 72 hours after BMSC encapsulation inside hosting oocytes. Fluorescence in the earlier post-injection hours (24 hours to 48 hours) did show much lower levels of green light emission, which corresponds to lower values of cell count: 74,000 cells/ml and 108,000/ml with viability 75% and 80% correspondingly.

Correlation between results of fluoroscopy and cell count can be explained only by presence of viable BMS cells inside recipient oocyte. In the control group, under the same fluorescent microscope, non-injected oocytes were not detectable, revealing in this case only monotonous black field.

Figure 5:
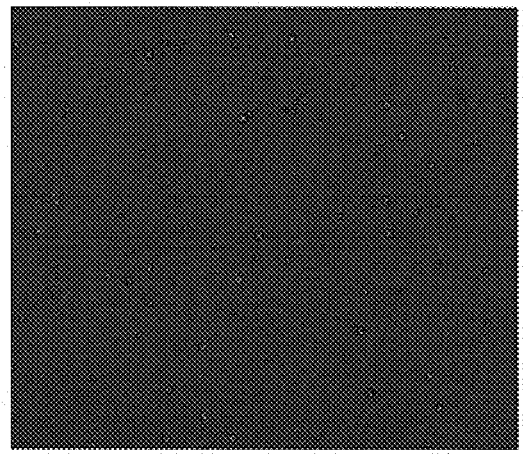
FIG. 5 shows BMSC in visual light 48 hours after encapsulation and 24 hours after removal from the oocyte (40× magnification).
Figure 6:
FIG. 6 shows a segment of the same culture plate shown in FIG. 5, under a fluorescent microscope (40× magnification). BMSC are evident.

The second step in the experiment was to establish material evidence that bone marrow stromal cells expressing GFP can survive and normally proliferate in vitro after injection procedure and subsequent encapsulation inside oocyte for 24+hours. FIG. 5 shows a population of tiny spherical cells in a culture plate 24 hours after BMSC were removed from frog ooplasm (where they stayed encapsulated for 48 hours). The removed cells exhibited perfect adherence to the culture dish. FIG. 6 shows a segment of the same plate under fluorescent microscope (filter #3).

Figure 7:
FIGS. 7–8 show "quark-cells" in visual light (FIG. 7) and under a fluorescent microscope (FIG. 8) after 24 hours of encapsulation and 48 hours after exhumation (40× magnification).
Figure 8:
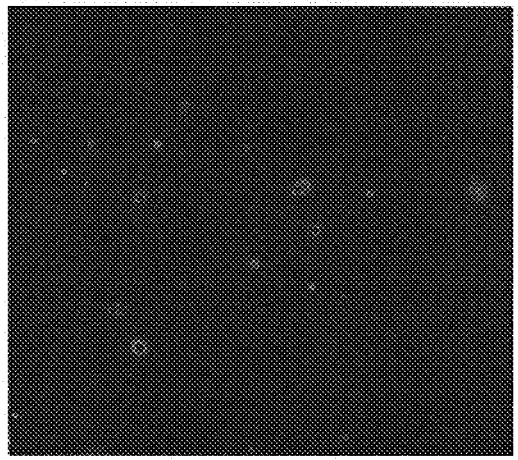

From this point, cells were maintained for another two weeks without any interference in regular culturing procedure. Growth media was replaced with fresh once every 3–4 days and cells were observed on a daily basis using a Zeiss invertoscope. FIGS. 7 and 8 show the same plates two weeks later. As can be seen in the figures, the round cells (former BMSC cells) now with more "confidence" retained their spherical shape and proliferation activity. Close similarity of these two micrographs and their fluoroscopic analogs (FIG. 6 and FIG. 8) indicates that by this time, the round cells with unknown destiny accomplished their geometrical and functional maturation. Observations conducted even two weeks later revealed no signs of confluency, which may indicate an exceptionally slow, idling type of proliferation. For reasons discussed later, these strange cells are referred to herein as a "quark-cells" or "bio-quarks".

Figure 9:
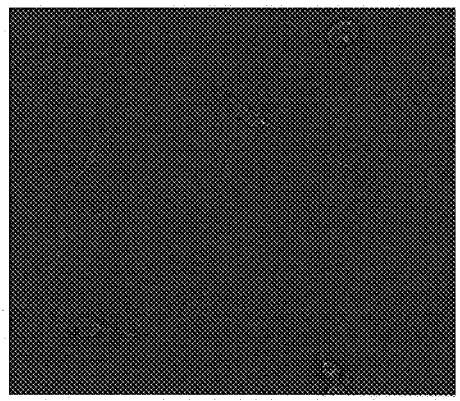
FIG. 9 shows control BMSC at 24 hours (20× magnification).
Figure 10:
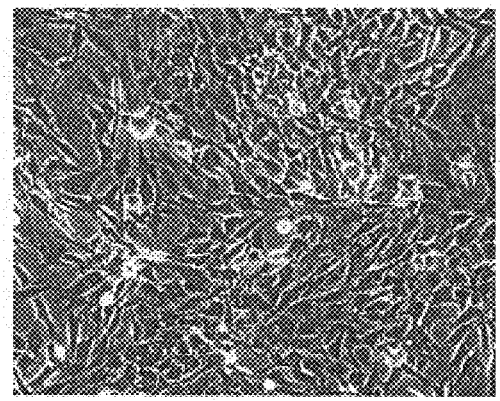
FIG. 10 shows confluent BMSC after 7 days (10× magnification).

Also, note a much smaller size and perfectly round shape of quark-cells (0.5–1 µm) and the absence of any other type of cells in FIG. 7 in comparison with cells in FIG. 9 representing control BMS cells (Ø±5 µm) at 24 hours of culturing, which never left the Petri dish for intra-oocyte encapsulation and also FIG. 10 (with courtesy of Dr. S. Song, University of South Florida, Department of Neurology), showing intact BMSC reaching confluency at the seventh day of culturing. Comparison of magnification scales between 40×FIG. 7, 20x FIG. 9, and 10x FIG. 10 makes differences in the sizes of quark-cells and BMSC more evident.

BMSC having a fibroblast-like appearance, which is typical of BMSC, are observed in FIG. 9 and FIG. 10, but are totally absent on FIG. 5 and FIG. 7. This may serve as direct evidence of intra-oocyte dedifferentiation of initial BMSC into sphere-like cells that are able to proliferate and express GFP. These cells appear to take a "wait-and-see attitude" mode, because these cells, as indicated above, could not reach confluency even by two weeks of culturing, and stayed at maximum cell amount calculated in these experiments of about 375,000 cells/ml with viability, as assessed by trypan blue viability test at 81%.

Figure 11:
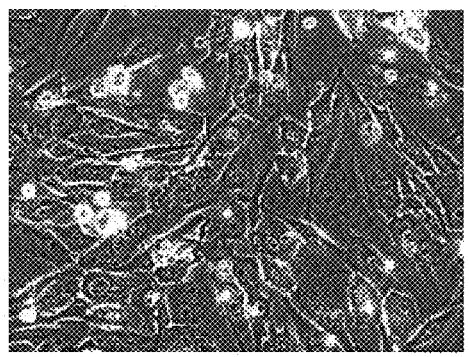
FIG. 11 shows SH-EP1 cells (control), which are cells of a human neuroepithelioma cell line.

Based on consumption, that bio-quarks even after two weeks of extra-oocyte culturing stay in the "waiting for guide to action" mode, $10^6$ cells/ml of human epithelial neuroblastoma cells SH-EP1 (embryonic tumor cells) (FIG. 11) as differentiation stimulating factor for "dormant" quark-cells were introduced into the dish with proliferation in the idle mode bio-quarks. The same amount of cells was added to the control dish, and one extra dish (quark cells only) was running in parallel as a control. Results of observations on "symbiotic" (quark-cells+SH-EP1 cells) plate after one week of join culturing, clearly shows development of multiple types of cells in FIG. 12 and on its fluorescent analog, FIG. 13.

Quark-cells in the control group in the absence of SH-EP1 cells remained in the "dormant" spherical state. Analyzing FIG. 12 and its fluoro-analog, FIG. 13, it is possible to conclude that SH-EP1 cells may trigger differentiation of bio-quarks into multiple types of cells, hence revealing their pluripotent nature.

Figure 12:
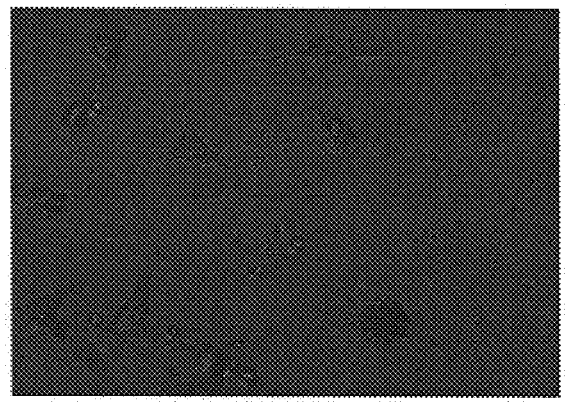
FIGS. 12–13 show micrographs of a "symbiotic" (quark-cells+SH-EP1 cells) plate after one week of culturing (40× magnification). Development of multiple types of cells is shown in FIG. 12 and its fluorescent analog, FIG. 13.
Figure 13:
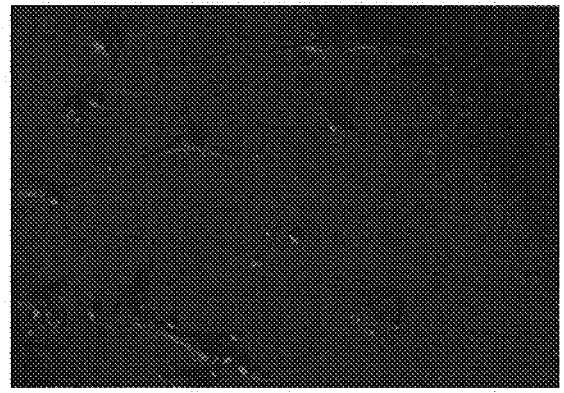
Figure 14:
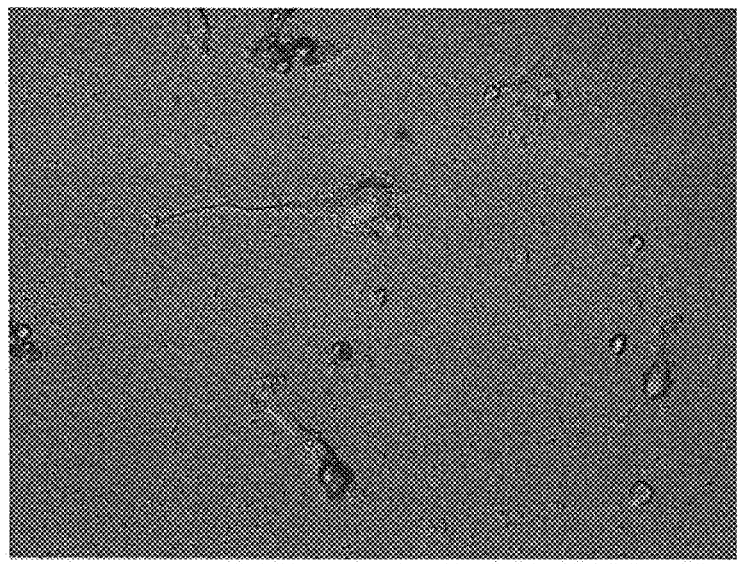
FIG. 14 shows a micrograph demonstrating cellular growth.
Figure 15:
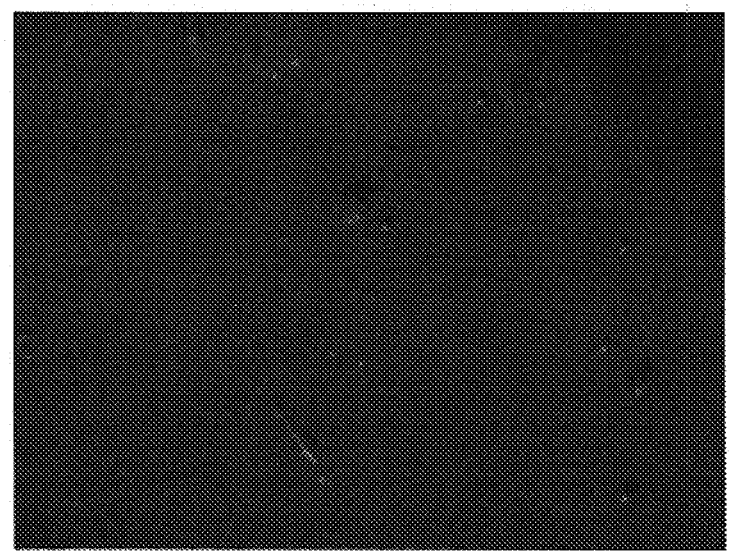
FIG. 15 shows a micrograph that is the fluorescent analog of FIG. 14.
Figure 16:
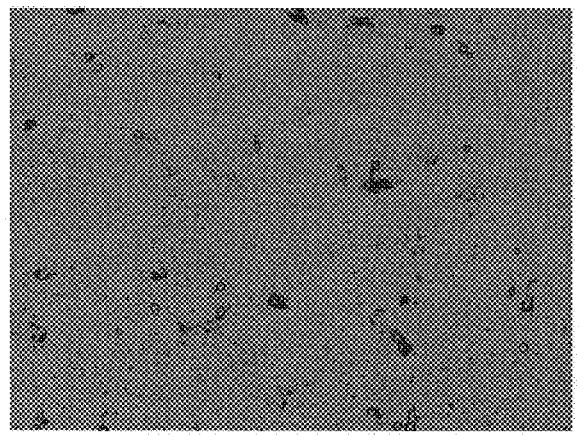
FIG. 16 shows a micrograph of the same area shown in FIG. 14 under lower magnification (20×), with a better view of the variety of cells present. There is a dramatic decrease in the number of SH-EP1 cells in comparison with the control group shown in FIG. 11.

Moreover, the SH-EP1 cells shown in FIG. 12 also show GFP-related green fluorescence, meaning that a nuclear fusion between quark-cells and SH-EP1 cells may be taking place, during which bio-quarks acquired certain knowledge of how to start to build different types of cells which is encoded inside chromatin of any somatic cell; in this case, a human neuroblastoma SH-EP1 cell, as a "teacher" cell. FIG. 14 and its fluorescent analog, FIG. 15, show another example of cellular growth.

Figure 17:
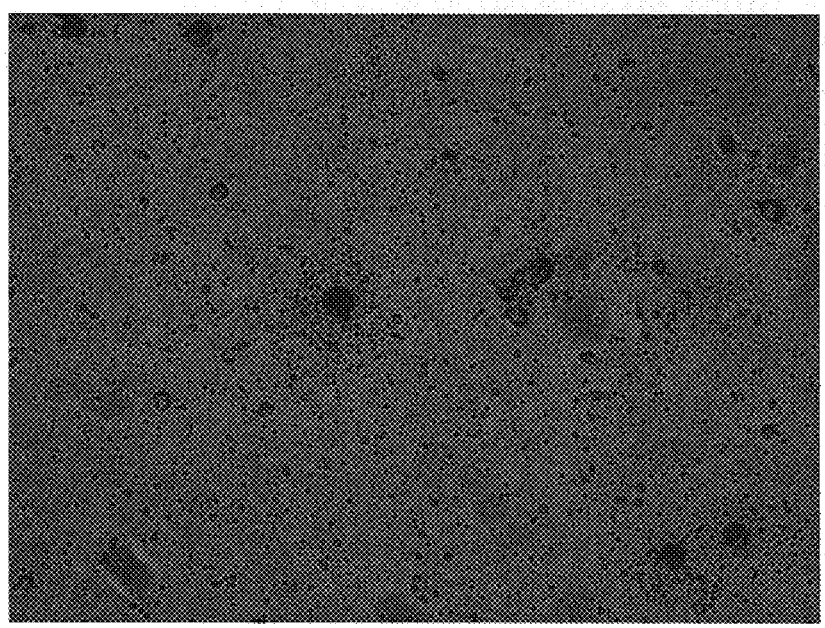
FIGS. 17–18 show two examples of areas of compression of quark-cells into "bio-galactic black holes" (40× magnification).
Figure 18:
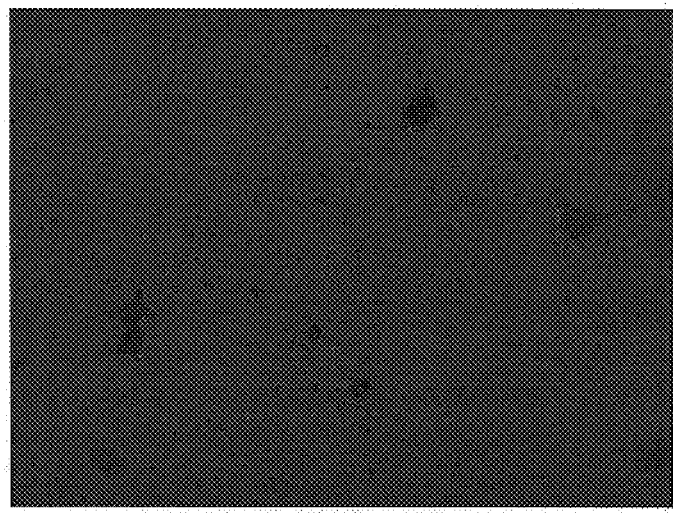

Careful analyses of more than 200 micrographs taken during preliminary experiments revealed that, after introduction of SH-EP1 cells as a stimulator, the quark-cells begin to act in an organized manner with a tendency to diminish in size and gather into dense clusters, which create a peculiar dark core (also referred to herein as a "black hole"). FIG. 17 and FIG. 18 show two examples of areas of compression of quark-cells into "bio-galactic black holes", from which the first image of the future cell seems to appear.

Figure 19:
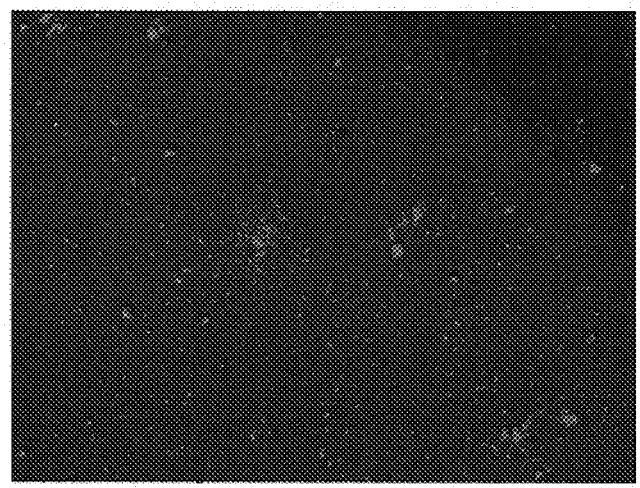
FIG. 19 shows a sector of the same area shown in FIG. 18, which clearly shows clusters of quark-cells under a fluorescent microscope.
Figure 20A:
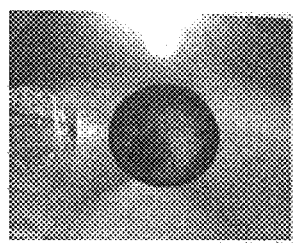
FIGS. 20A–D show different 44 day old oocytes seated in recording chambers of Opus-Express equipment before the experiment. Surprisingly, despite a very asymmetric, interpenetrative appearance of vegetal and animal parts in aged oocytes, they were able to successfully express functionally active $\alpha_4/\beta_2$ HNR.
Figure 20B:
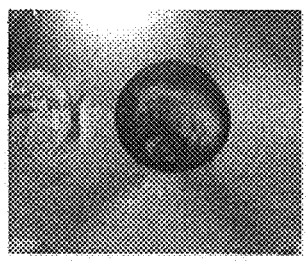
Figure 20C:
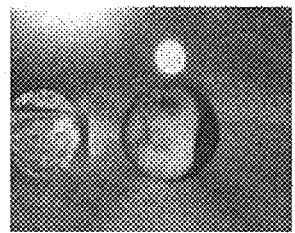
Figure 20D:
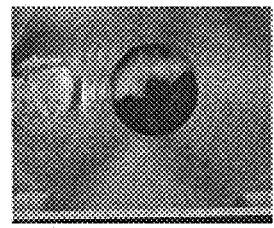

FIG. 19 shows a sector of the same area as shown in FIG. 18 which clearly shows clusters of quark-cells under fluorescent microscope with myriads of restless bio-quarks harboring the life. The molecular composition and mechanisms of origin of the hazy "nebulas" shown in FIG. 18 is unclear. They can be seen only in the field of visual light and not under fluorescent microscope. "Nebulas" appear only after introduction of SH-EP1 cells and may consist of a fine informational substance which is able to send a quark-cell-specific signals summoning them to start local compression, which creates in that area a dark core or "black hole" at that, darker the "hole"-more bio-quarks are attracted. As can be seen, in this process at certain point may lead to formation of embryonic stem cell. Apparently, presence of SH-EP1 cells or any other type of differentiated somatic cell is mandatory for creation of "nebulas" and activation of "dormant" quark-cells.

EXAMPLE 2

Survival and Function of BMSC within *Xenopus laevis* Oocytes

Finally, the last set of experiments was devoted to the study of the longevity of recipient oocytes with control test for their functional activity in the form of ability of oocytes to express $\alpha_4/\beta_2$ subunits of human nicotinic receptors in their membranes 48h after RNA injection.

This investigation yielded fascinating results: BMSC injected oocytes which were carefully maintained in the appropriate incubation buffer were able to survive for 44 days (then experiment was terminated, because of electrophysiological recordings) while non-injected oocytes lived only 21 days. It means that injected oocytes outlived the oocytes in the control group more than twice. FIGS. 20A–20D show different 44 day old oocytes seated in the recording chambers of Opus-Express equipment before the experiment. As is evident from FIGS. 20A–20D, the appearance of aged oocytes are sharply different from those in the beginning of incubation (FIG. 2).

Figure 21:
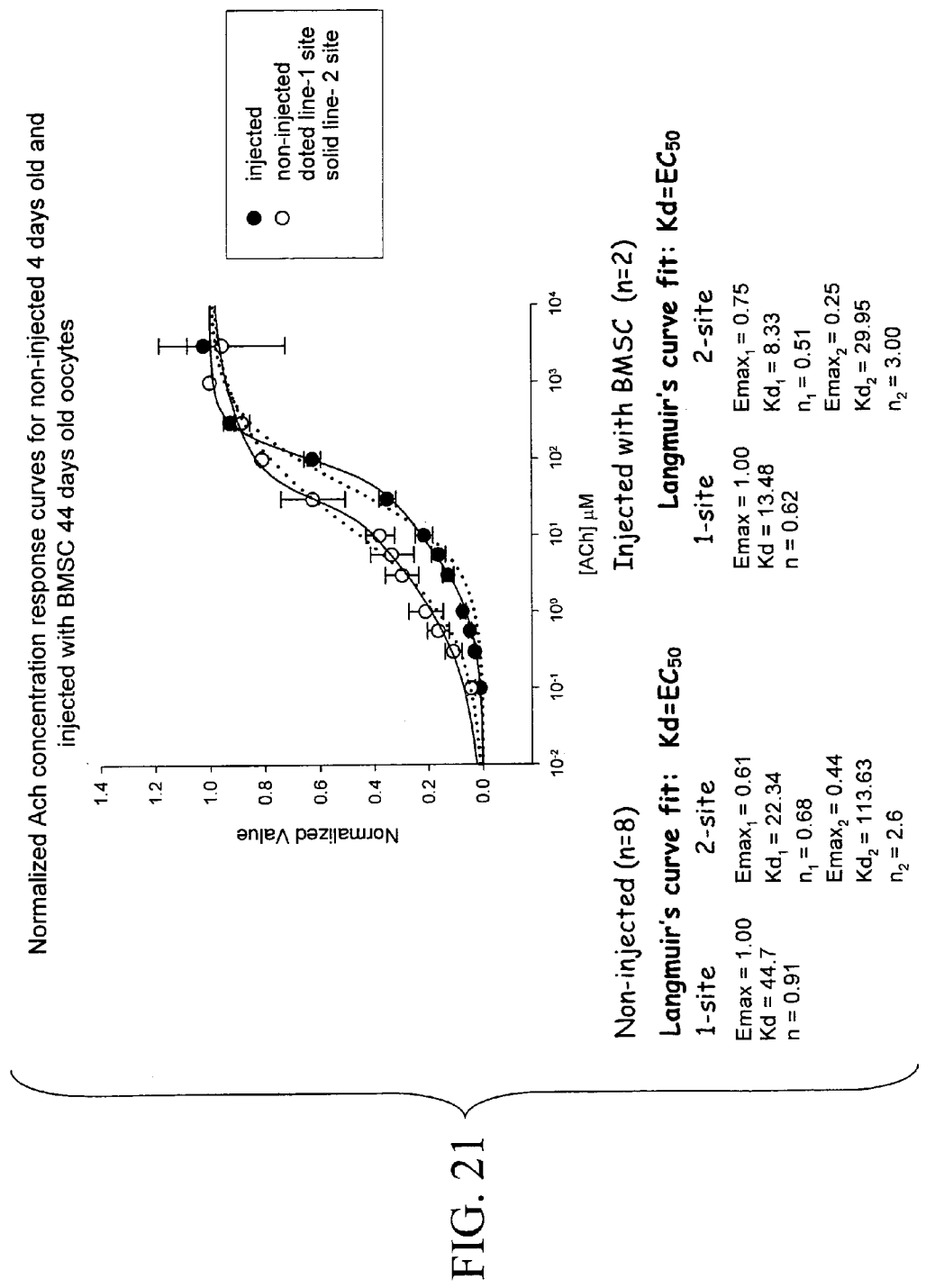
FIG. 21 shows acetylcholine chloride concentration response curves for 44 day old oocytes injected with BMSC, and response curves for non-injected oocytes.

During process of recordings four out of six BMSC injected oocytes taken into this set of experiments showed very high expression of receptors with off scale currents which were not properly recorded because of initial voltage-gain settings and suddenness of effect. Fortunately, rest two oocytes showed logged currents through entire experiment. Comparison of two normalized dose response curves (shown in FIG. 21) reveals better logistic fit with 2 site Langmuir's curve fit analysis (solid lines) then with 1 site (dotted lines) for both set of experiments.

A better fit in each case was obtained with the sum of two Hill equations yielding high-affinity coefficients of $EC_{50}H=22.34$ µM and $nH1=0.68$ and low-affinity values of $EC_{50}L=113.63$ µM and $nH2=2.6$ for non-injected control oocytes and high-affinity coefficients of $EC_{50}H=8.331$M and $nH1=0.51$ and low-affinity of $EC_{50}L=29.95$ µM and $nH2=3.0$ for injected with BMSC recipient eggs. It means that for high-affinity sites of $\alpha_4/\beta_2$ subunits of HNR BMSC injected oocytes in comparison with oocytes in the control group can achieve 50% of Ach evoked peak current amplitude at 2.7 times lower concentration of agonist, while with same tendency, for low affinity sites 50% of peak current can reach at 3.8 times lower concentration of Ach. These results may indicate that biochemical machinery of expression of $\alpha_4/\beta_2$ subunits of HNR in BMSC injected oocytes despite of their senile age works more efficiently then same mechanisms in non-injected frog oocytes. It means that BMSC injected, quark-cell contained oocytes in some experiments may be used as a peculiar high expression machine for hard-to-express receptors, for example, such as $\alpha 7$ subunit of HNR.

With use of this new technique, small cells (up to 15 µm in diameter) on the example of BMSC derived from Tg-mice can be injected into *Xenopus laevis* oocyte without critical damage to the membrane, and without compromising the survival and integrity of the hosting oocyte. Bone marrow stromal cells after encapsulation inside oocytes for 24–48 hours can be removed from the ooplasm and successfully cultured in appropriate media with good adherence to the bottom of culture plate. The manner of culturing (with centrifugation or without centrifugation) has no influence on the pattern of cell adherence and proliferation in the culture dish. After "exhumation" from the oocyte, BMSC have never been detected again. This is apparently because BMSC irreversibly dedifferentiated into tiny (0.5 µm) spherical cells referred to herein as quark-cells, which can grow and proliferate in the culture plate without any signs of confluency. This may indicate the existence of mechanisms which control and balance the birth/death ratio in the culture, not allowing the death of quark-cells to prevail over their birth, and vice versa, which is very important.

In the working examples described herein, it is evident that the quark-cells are descendants of BMSC injected into oocytes because this is what was exhumed from oocytes after injection and encapsulation. Moreover, continued expression of GFP by quark-cells reveals their direct links to BMSC.

Stabilized in the "wait-and-see attitude" mode by the birth/death balance mechanism, bio-quarks can be triggered to differentiate into different types of cells by adding human neuroblastoma SH-EP1 cells (which are tumor cells) to the culture of quark-cells.

Quark cells interact with SH-EP 1 cells in a way that dramatically inhibits the growth of malignant cells. Simultaneously, this interaction switches bio-quarks from their dormant condition to an active state of pluripotency. Before quark-cells start to differentiate under the influence of SH-EP1 cells, they begin to diminish in size in FIG. 18. In FIG. 19, in comparison with FIG. 7 and FIG. 8, they look much smaller. This means that during an "intervention" of SH-EP1 cells quark-cells undergo substantial shrinkage in size before they start the process of compression into "black holes".

Since bio-quarks retain their ability to emit green fluorescence it would be desirable to obtain a quality micrographs of quark-cells under the higher magnification to determine if they also retain their morphological integrity as a whole cell. Otherwise, it should be considered whether bio-quarks are a tiny, bacteria-like living organism ad exemplum *Mycoplasma genitalium*—the smallest known living thing in the world, with its only 480 protein-coding genes essential for phenomenon of life, including about 100 genes of unknown function.

Quark-cells, for some reason, retain the GFP chromophore peptide gene encoding the amino acid sequence Phe-Ser-Tyr-Gly-Val-Gin (SEQ ID NO: 1) of hexapeptide from jellyfish Aequorea victoria GFP, which is unique among fluorescent proteins in that its fluorophore is not a separately synthesized prosthetic group but composed of modified amino acid residues within the polypeptide chain. However, no matter how small quark-cells become in the process of preparing for their differentiation into another type of cell, or how important their participation in the construction of new cellular structures is in the culture dish, they always carry fluorescence with them. This phenomenon should be investigated further, particular in the connection with mechanisms of operation of genes with unknown function which can be essential for origins of life.

Since BMSC irreversibly dedifferentiate during their encapsulation inside oocytes, converting their shape and function into those of quark-cells, results of lifespan studies are mostly due to unknown action of bio-quarks which somehow can affect the mechanisms, underlying the processes of aging in the *Xenopus* oocyte. Results of electrophysiological studies shows that the presence of quark-cells inside oocytes for long periods of time (e.g., 44 days) increases the capability of oocytes to express $\alpha 4/\beta 2$ subunits of HNR, thus promising to be an efficient factory for production of hard-to-express membrane proteins, such as $\alpha 7$ HNR, for example.

The cell within a cell (or cell-inside-cell) model of the present invention can be a powerful method of dedifferentiation of adult BMSC into absolutely spherical quark-cells with a yet to be determined micro-morphological structure, biochemical properties, and function. Nevertheless, this new technique should allow investigators, for the first time, to inject suspensions of small cells inside a larger cell. This method may represent a new methodological approach not only in stem cell therapy but also in many other areas of biological science. Based on the results of preliminary studies, the next step of primary importance is to identify quark cells and all other cells present in the culture plate as a resultant of interaction between bio-quarks and SH-EP1 cells using such powerful analytical tools in molecular biology as: detection of cell surface antigens using CD markers; detection of neuron specific proteins; assessment of the status of cell division using a BrdU assay; measurement of telomerase activity and expression of Oct-4 gene in the cells of interest, bio-quarks, etc. Finally, it is important to evaluate intra-oocyte injection of different types of somatic cells, including cancer cells, to see if they also can dedifferentiate into non-pathologic, biologically active spherical units, called quarks-cells, which apparently are unique and essential for life and cell rejuvenation.

TABLE 1

Examples of Target Cells for Encapsulation

Keratinizing Epithelial Cells keratinocyte of epidermis
basal cell of epidermis
keratinocyte of fingernails and toenails
basal cell of nail bed
hair shaft cells medullary
cortical
cuticular
hair-root sheath cells cuticular
of Huxley's layer
of Henle's layer
external
hair matrix cell TABLE 1-continued Examples of Target Cells for Encapsulation Cells of Wet Stratified Barrier Epithelia surface epithelial cell of stratified squamous epithelium of cornea tongue, oral cavity, esophagus, anal canal, distal urethra, vagina
basal cell of these epithelia
cell of urinary epithelium
Epithelial Cells Specialized for Exocrine Secretion cells of salivary gland mucous cell
serous cell
cell of von Ebner's gland in tongue
cell of mammary gland, secreting milk
cell of lacrimal gland, secreting tears
cell of ceruminous gland of ear, secreting wax
cell of eccrine sweat gland, secreting glycoproteins
cell of eccrine sweat gland, secreting small molecules
cell of apocrine sweat gland
cell of gland of Moll in eyelid
cell of sebaceous gland, secreting lipid-rich sebum
cell of Bowman's gland in nose
cell of Brunner's gland in duodenum, secreting alkaline solution of mucus and enzymes
cell of seminal vesicle, secreting components of seminal fluid, including fructose
cell of prostate gland, secreting other components of seminal fluid
cell of bulbourethral gland, secreting mucus
cell of Bartholin's gland, secreting vaginal lubricant
cell of gland of Littré, secreting mucus
cell of endometrium of uterus, secreting mainly carbohydrates
isolated goblet cell of respiratory and digestive tracts, secreting mucus
mucous cell of lining of stomach
zymogenic cell of gastric gland, secreting pepsinogen
oxyntic cell of gastric gland, secreting HCl
acinar cell of pancreas, secreting digestive enzymes and bicarbonate
Paneth cell of small intestine, secreting lysozyme
type II pneumocyte of lung, secreting surfactant
Clara cell of lung
Cells Specialized for Secretion of Hormones cells of anterior pituitary, secreting growth hormone
follicle-stimulating hormone
luteinizing hormone
prolactin
adrenocorticotropic hormone
thyroid-stimulating hormone
cell of intermediate pituitary, secreting melanocyte-stimulating hormone
cells of posterior pituitary, secreting oxytocin
vasopressin
cells of gut and respiratory tract, secreting serotonin
endorphin
somatostatin
gastrin
secretin
cholecystokinin
insulin
glucagons
bombesin
cells of thyroid gland, secreting thyroid hormone
calcitonin
cells of parathyroid gland, secreting parathyroid hormone
oxyphil cell
cells of adrenal gland, secreting epinephrine
norepinephrine TABLE 1-continued Examples of Target Cells for Encapsulation steroid hormones mineralocorticoids
glucocorticoids
cells of gonads, secreting testosterone
estrogen
progesterone
cells of juxtaglomerular apparatus of kidney juxtaglomerular cell
macula densa cell
peripolar cell
mesangial cell
Epithelial Absorptive Cells in Gut, Exocrine Glands, and Urogenital Tract brush border cell of intestine
striated duct cell of exocrine glands
gall bladder epithelial cell
brush border cell of proximal tubule of kidney
distal tubule cell of kidney
nonciliated cell of ductulus efferens
epididymal principal cell
epididymal basal cell
Cells Specialized for Metabolism and Storage hepatocyte
fat cells (e.g., adipocyte)

white fat
brown fat
lipocyte of liver
Epithelial Cells Serving Primarily a Barrier Function, Lining the Lung, Gut, Exocrine Glands, and Urogenital Tract type I pneumocyte
pancreatic duct cell
nonstriated duct cell of sweat gland, salivary gland, mammary gland, etc.
parietal cell of kidney glomerulus
podocyte of kidney glomerulus
cell of thin segment of loop of Henle
collecting duct cell
duct cell of seminal vesicle, prostate gland, etc.
Epithelial Cells Lining Closed Internal Body Cavities vascular endothelial cells of blood vessels and lymphatics (e.g., microvascular cell)

fenestrated
continuous
splenic
synovial cell
serosal cell
squamous cell lining perilymphatic space of ear
cells lining endolymphatic space of ear squamous cell
columnar cells of endolymphatic sac with microvilli
without microvilli
"dark" cell
vestibular membrane cell
stria vascularis basal cell
stria vascularis marginal cell
cell of Claudius
cell of Boettcher
choroid plexus cell
squamous cell of pia-arachnoid
cells of ciliary epithelium of eye pigmented
nonpigmented
corneal "endothelial" cell TABLE 1-continued Examples of Target Cells for Encapsulation Ciliated Cells with Propulsive Function of respiratory tract
of oviduct and of endometrium of uterus
of rete testis and ductulus efferens
of central nervous system
Cells Specialized for Secretion of Extracellular Matrix epithelial:

ameloblast
planum semilunatum cell of vestibular apparatus of ear
interdental cell of organ of Corti
nonepithelial:

fibroblasts
pericyte of blood capillary (Rouget cell)
nucleus pulposus cell of intervertebral disc
cementoblast/cementocyte
odontoblast/odontocyte
chondrocytes of hyaline cartilage
of fibrocartilage
of elastic cartilage
osteoblast/osteocyte
osteoprogenitor cell
hyalocyte of vitreous body of eye
stellate cell of perilymphatic space of ear
Contractile Cells skeletal muscle cells red
white
intermediate
muscle spindle-nuclear bag
muscle spindle-nuclear chain
satellite cell
heart muscle cells ordinary
nodal
Purkinje fiber
Cardiac valve tissue
smooth muscle cells
myoepithelial cells:

of iris
of exocrine glands
Cells of Blood and Immune System red blood cell (erythrocyte)
megakaryocyte
macrophages monocyte
connective tissue macrophage
Langerhan's cell
osteoclast
dendritic cell
microglial cell
neutrophil
eosinophil
basophil
mast cell
plasma cell
T lymphocyte helper T cell
suppressor T cell
killer T cell
B lymphocyte IgM
IgG
IgA TABLE 1-continued Examples of Target Cells for Encapsulation IgE
killer cell
stem cells and committed progenitors for the blood and immune system
Sensory Transducers photoreceptors rod
cones blue sensitive
green sensitive
red sensitive
hearing inner hair cell of organ of Corti
outer hair cell of organ of Corti
acceleration and gravity type I hair cell of vestibular apparatus of ear
type II hair cell of vestibular apparatus of ear
taste type II taste bud cell
smell olfactory neuron
basal cell of olfactory epithelium
blood pH carotid body cell type I
type II
touch Merkel cell of epidermis
primary sensory neurons specialized for touch
temperature primary sensory neurons specialized for temperature cold sensitive
heat sensitive
pain primary sensory neurons specialized for pain
configurations and forces in musculoskeletal system proprioceptive primary sensory neurons
Autonomic Neurons cholinergic
adrenergic
peptidergic
Supporting Cells of Sense Organs and of Peripheral Neurons supporting cells of organ of Corti inner pillar cell
outer pillar cell TABLE 1-continued Examples of Target Cells for Encapsulation inner phalangeal cell
outer phalangeal cell
border cell
Hensen cell
supporting cell of vestibular apparatus
supporting cell of taste bud
supporting cell of olfactory epithelium
Schwann cell
satellite cell
enteric glial cell
Neurons and Glial Cells of Central Nervous System neurons
glial cells astrocyte
oligodendrocyte
Lens Cells anterior lens epithelial cell
lens fiber
Pigment Cells melanocyte
retinal pigmented epithelial cell
iris pigment epithelial cell
Germ Cells oogonium/oocyte
spermatocyte
Spermatogonium
blast cells
fertilized ovum
Nurse Cells ovarian follicle cell
Sertoli cell
thymus epithelial cell (e.g., reticular cell)
placental cell All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A microincubator comprising an isolated host *Xenopus laevis* oocyte having at least one bone marrow stromal (BMS) cell encapsulated within the cytoplasm of the host oocyte.

2. The microincubator of claim 1, wherein said at least one encapsulated BMS cell is one BMS cell.

3. The microincubator of claim 1, wherein said at least one encapsulated BMS cell comprises at least one human BMS cell.

4. The microincubator of claim 1, wherein said at least one encapsulated BMS cell comprises at least one mouse BMS cell.

5. The microincubator of claim 1, wherein said at least one BMS cell has been genetically modified.

6. A method for making a microincubator, comprising introducing at least one bone marrow stromal (BMS) cell into the cytoplasm of an isolated *Xenopus laevis* oocyte.

7. The method of claim 6, wherein the at least one BMS cell is one BMS cell.

8. The method of claim 4, wherein the at least one BMS cell comprises at least one human BMS cell.

9. The method of claim 6, wherein the at least one BMS cell comprises at least one human BMS cell.

10. The method of claim 6, wherein the at least one BMS cell has been genetically modified prior to said introducing.

* * * * *

UNITED STATES PATENT AND TRADEMARK OFFICE
CERTIFICATE OF CORRECTION

| | | |
|---|---|---|
| PATENT NO. | : 7,135,336 B1 | Page 1 of 1 |
| APPLICATION NO. | : 11/109311 | |
| DATED | : November 14, 2006 | |
| INVENTOR(S) | : Sergei Paylian | |

It is certified that error appears in the above-identified patent and that said Letters Patent is hereby corrected as shown below:

<u>Title page, (54), and column 1, line 1</u>
"Use of *Xenopus Laevis* Oocytes a Microincubators" should read --Use of *Xenopus Laevis* Oocytes as Microincubators--.

<u>Column 16,</u>
Line 24, "40xFIG. 7," should read --40x Figure 7,--.

<u>Column 17,</u>
Line 62, "$EC_{50}H=8.331M$" should read --$EC_{50}H=8.33\mu M$--.

<u>Column 26,</u>
Line 15, "of claim 4" should read --of claim 6--.

Line 18, "one human BMS cell" should read --one mouse BMS cell--.

Signed and Sealed this

Twenty-second Day of May, 2007

JON W. DUDAS
*Director of the United States Patent and Trademark Office*

SEQUENCE LISTING

```
<160> NUMBER OF SEQ ID NOS: 1

<210> SEQ ID NO 1
<211> LENGTH: 6
<212> TYPE: PRT
<213> ORGANISM: Aequorea victoria
```

-continued

```
<400> SEQUENCE: 1

Phe Ser Tyr Gly Val Gln
1               5
```